United States Patent [19]

Nelson

[11] 4,068,665
[45] Jan. 17, 1978

[54] DISPOSABLE DIAPER WITH IMPROVED TAPE FASTENER

[75] Inventor: Lawrence E. Nelson, Vader, Wash.

[73] Assignee: Weyerhaeuser Company, Tacoma, Wash.

[21] Appl. No.: 747,589

[22] Filed: Dec. 6, 1976

[51] Int. Cl.² ............................................. A61F 13/16
[52] U.S. Cl. .................................... 128/287; 128/284
[58] Field of Search ................................. 128/284, 287

[56] References Cited

U.S. PATENT DOCUMENTS

| | | | |
|---|---|---|---|
| 3,758,363 | 9/1973 | Frick | 128/287 |
| 3,848,594 | 11/1974 | Buell | 128/284 |
| 3,985,136 | 10/1976 | Cepuritis | 128/287 |
| 3,990,449 | 11/1976 | Cheslow | 128/287 |
| 4,002,172 | 1/1977 | Feldman | 128/284 |

*Primary Examiner*—Aldrich F. Medbery

[57] ABSTRACT

An improved diaper fastener system has particular application to a disposable diaper having a generally rectangular-shaped absorbent pad or filler disposed between a fluid-permeable cover sheet and a thermoplastic film backing sheet. The fastener system is comprised of a pair of pressure-sensitive fastening tapes incorporaing a standard release liner with each tape. The improvement includes anchoring one surface of the fixed portion of the fastening tape of the bottom surface of the cover sheet and then adhesively bonding the other surface of the fixed portion to a folded-over side marginal portion of the backing sheet. The release liner is positioned atop the cover sheet and extends laterally a distance that corresponds with the lateral dimension of the attachment portion of the tape. When the tape fastener system is in its closed position, the attachment portion of the tape lies against the release liner and when it is in the open position, the attachment portion extends outwardly from the side edge of the diaper and any forces that are applied to the tape are then transferred to the top cover sheet which is stronger than the plastic film backing sheet.

2 Claims, 6 Drawing Figures

DISPOSABLE DIAPER WITH IMPROVED TAPE FASTENER

BACKGROUND OF THE INVENTION

This invention relates generally to disposable diapers and more particularly to an improved tape fastener system for such diapers.

Conventional disposable diapers in one popular construction are comprised of the generally rectangular absorbent pad or filler disposed between a fluid-permeable body facing top sheet and a fluid-impermeable plastic film backing sheet. The filler may be comprised of standard commercially available fluff pulp while the top sheet may be comprised of a standard commercially available nonwoven material and the backing sheet may be comprised of a thin sheet of polyethylene. At the lateral side edges of the diaper the backing sheet can be folded around the edges and sealed so that a narrow strip overlies the top sheet while at the ends of the diaper the top sheet and backing sheet can extend loosely past the top and bottom edges of the filler while being bonded together, providing a foldable flap to tuck in against the top sheet upon diapering.

A tape fastener system, in a standard construction, is comprised of a pair of pressure-sensitive fastening tapes that are adhered to the backing sheet at one end of the diaper. Usually the tapes are comprised of two separate parts with one part being the fastening tape having a fixed portion permanently bonded to the backing sheet, while the other end is the attachment portion and extends in the closed position around the side edge to overlie the separate release liner which is adhesively bonded to the top sheet. When ready for use, the attachment portion of the tape is removed from the release liner and pulled so as to extend outwardly from the side edge, thereby pulling on the plastic backing sheet with the typically exerted attaching and in-use forces.

A major problem with standard tape fastener systems that are anchored to the plastic backing sheet is when a person applies tension to the tape, stresses are created within the plastic film that often cause the film to rupture and tear, making the diaper unusable. This problem has been recognized and at least three solutions have been proposed. One solution may be seen by referring to U.S. Pat. No. 3,867,940 issued Feb. 25, 1975 to Mesek et al wherein a reinforcing scrim having a higher modulus of elasticity than the plastic film backing sheet is adhered to the thin film in a location in at least the vicinity of where the tape is adhered to the thin film. This construction allows some of the stress to be accepted by the stronger reinforcing material. Another solution may be seen by referring to U.S. Pat. No. 3,900,031 issued Aug. 19, 1975 to Endres et al, in which the fastening tapes are attached to the backing sheet in an area where the top sheet is adhered thereto along the entire top edge. In the Endres et al construction, the filler material terminates so that it does not extend all the way in a longitudinal direction to the sealed top end margin of the diaper. A third solution may be seen by referring to U.S. Pat. No. 3,848,594 issued Nov. 19, 1974 to Buell in which the attachment portion is joined to a secondary tape which is then bonded to at least part of the top cover sheet creating an area of joinder adjacent the edge of the diaper so that forces imposed on the attachment portion of the tape are transmitted to both the front and back surfaces of the diaper. Each of these tape fastener constructions operate to solve the rupturing problem for a particular diaper construction; however, other solutions for various reasons are continually being sought and the present invention is another solution unlike those known in the art.

Accordingly, from the foregoing, one object of the present invention is to provide an improved diaper fastener system that reduces or eliminates tearing of the plastic film backing sheet.

Another object of the invention is to provide a diaper tape fastener system that is economical to manufacture and easy to incorporate in the diaper.

Still a further object of the present invention is to reduce tearing of the plastic backing sheet while still substantially retaining a conventional disposable diaper structure.

These and other objects of the invention will become more apparent upon reading the description to follow while referring to the drawings.

SUMMARY OF THE INVENTION

Briefly stated, this invention is comprised in one form of a disposable diaper of a type having a generally rectangular absorbent pad or filler disposed between a fluid-permeable body contacting top sheet and a fluid-impermeable plastic film backing sheet together with a pair of tape fastener systems. A tape fastener system is comprised of two parts, the first part being the actual fastening tape having an attachment portion and a fixed portion, with the second part being the standard release liner for holding the attachment portion when in the closed position. Unlike prior art diaper tape fastener systems, the fastening tape is fixed along one surface of the fixed portion to the bottom surface of the top sheet and is adhesively bonded along the opposite surface of the fixed portion to a portion of the plastic backing sheet. In the open position, the attachment portion of the tape will extend outwardly from the side edge of the diaper and when force is exerted thereon it will be primarily transmitted to the top sheet while leaving the weaker backing sheet material essentially unstressed, thereby preventing rupturing of the plastic backing sheet. The typical release liner is fixed to the top surface of the top sheet in its normal position so that when the fastening tape is in the closed position the adhesive side of the attachment portion will overlie the release surface of the release liner.

DESCRIPTION OF THE PREFERRED EMBODIMENTS

Figure 1:
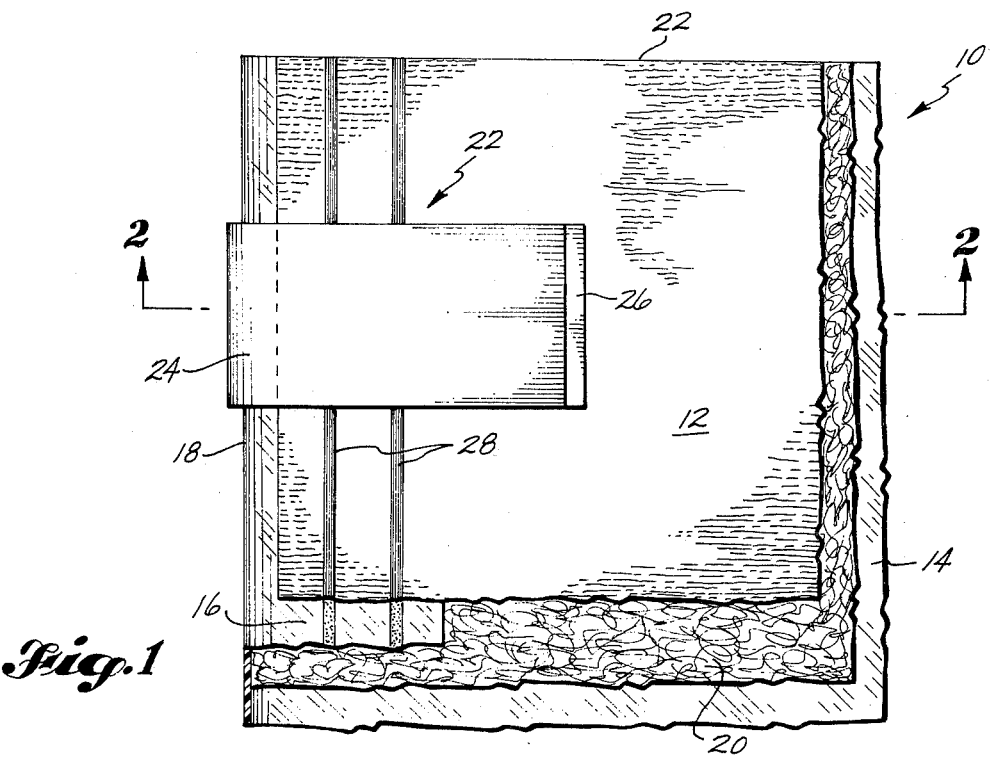
FIG. 1 is a cutaway plan view of one corner of a disposable diaper incorporating the tape fastener system of the present invention and showing it in its closed position.

Referring first to FIG. 1, a brief general description will be given of the disposable diaper suitable for use with the present invention. A cutaway portion of a generally rectangular disposable diaper is indicated at 10. The typical disposable diaper 10 is comprised of a liquid-permeable body contacting top sheet 12 which is the size of the diaper's rectangular planar area and is normally comprised of, for example, a typical thin nonwoven material having relatively high cross-directional strength. The backing sheet 14 is comprised of a liquid-impermeable thin thermoplastic material such as polyethylene and is generally the same size as top sheet 12, with a standard exception being the top side marginal portions 16 which are folded around the side edges 18 and then bonded in place. Disposed between the top sheet 12 and backing sheet 14 is the substantially rectangular absorbent pad or filler 20. The filler 20 may be comprised of any suitable liquid absorbing material such as, for example, typical commercially available fluff pulp. Along the top and bottom marginal edges 22 the top sheet and backing sheet material are bonded together to enclose filler material 20.

Figure 2:
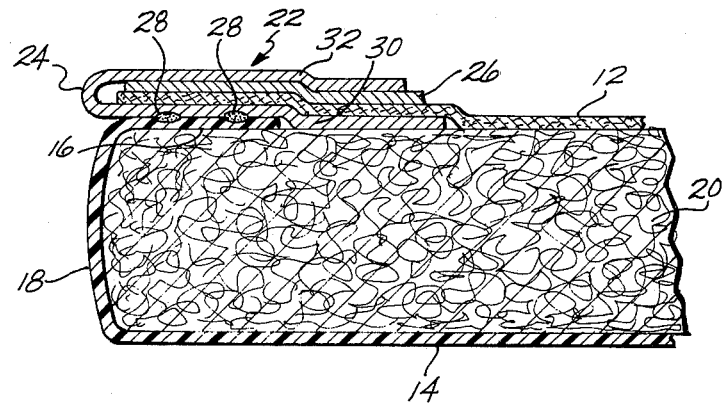
FIG. 2 is a cross-section taken along line 2—2 of FIG. 1 and shows the details of the tape fastener structure.

Turning now to a specific description of the tape fastener system comprising the present invention, reference will be made to FIGS. 1-3 for a description of one preferred embodiment. One of a pair of tape fasteners comprising the tape fastener system is generally indicated at 22. The other fastener of the pair would be positioned laterally oposite the one shown and would be constructed in the same manner. Tape fastener 22 is typical in that it is comprised of a pressure-sensitive fastening tape 24 together with a typical release liner 26. In the present diaper construction, the top sheet 12 extends laterally to each side edge 18 of diaper 10 while the backing sheet 14, in constructing the top side marginal portions 16, is positioned so as to underlie the top sheet material along each side edge. Suitable adhesive means 28 join the top side marginal portion 16 of the backing sheet material to the lateral edges of the overlying top sheet material. At the areas where the fastening tapes 24 are attached to diaper 10 the fixed portion 30 of fastening tapes 24 are positioned so as to underlie the lateral side edge of the top sheet 12 and overlie the side marginal portion 16 of the backing sheet material. The upper surface of fixed portion 30 underlying the top sheet material is an adhesive surface and is therefore fixedly attached to the top sheet lower surface. The adhesive means 28 serve to fixedly attach the side marginal portions 16 to the lower surface of the fixed portions 30. The attachment portions 32 of fastening tapes 24 are then folded over 180° overlie the release surface of its release liner 26 which is fixedly attached to the top surface of top sheet 12.

Figure 3:
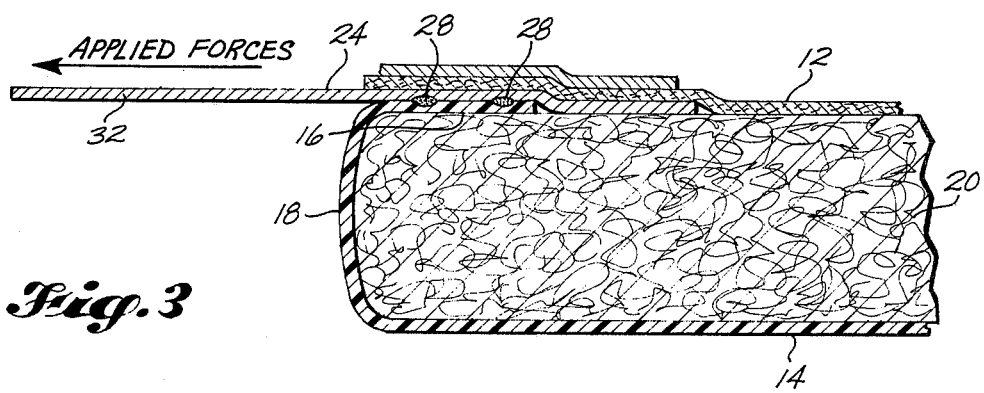
FIG. 3 is a view similar to FIG. 2 but shows the attachment portion of the fastening tape extending outwardly from the side edge of the diaper and under a stressed condition.

When the individual who will be diapering the infant is ready to apply the diaper and use tape fasteners 22, that individual will simply peel the attachment portions 32 of tapes 24 away from the release liner and begin exerting the forces on it as depicted in FIG. 3. These in-use forces will be exerted as the person positions the diaper about the infant and pulls the waist portion tight. The forces will be transmitted primarily to the top sheet 12 at each tape fastener 22 through the attachment between fixed portion 30 and the bottom juxtaposed surface of the top sheet. By so transferring the forces, the majority of force is accepted by the stronger top sheet material rather than the weaker backing sheet material. Tearing and rupturing of the backing sheet material is thereby effectively prevented.

Figure 4:
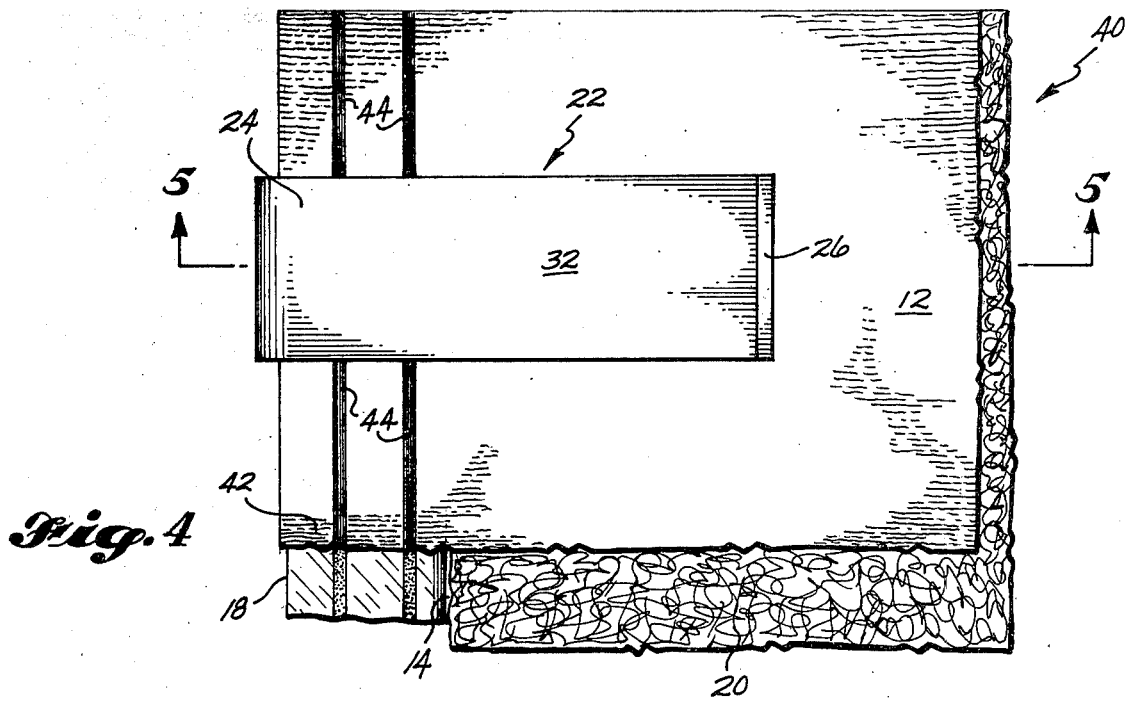
FIG. 4 is a view similar to FIG. 1 but shows an alternate embodiment of the present invention.
Figure 5:
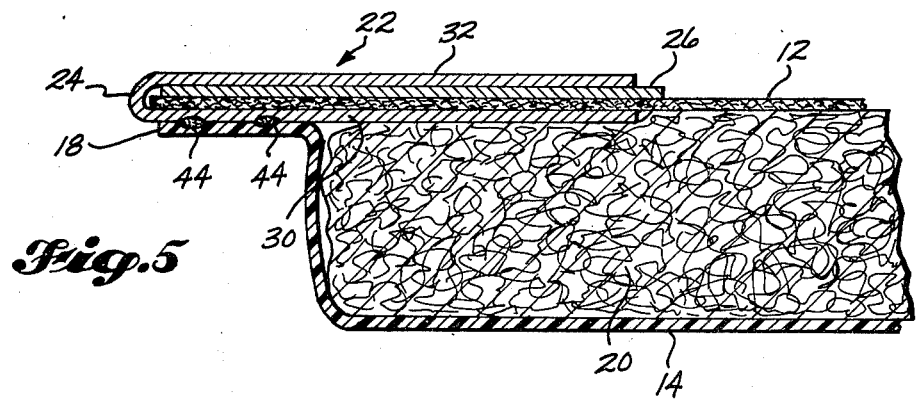
FIG. 5 is a view similar to FIG. 2 taken along line 5—5 of FIG. 4 showing the details of the alternate embodiment.
Figure 6:
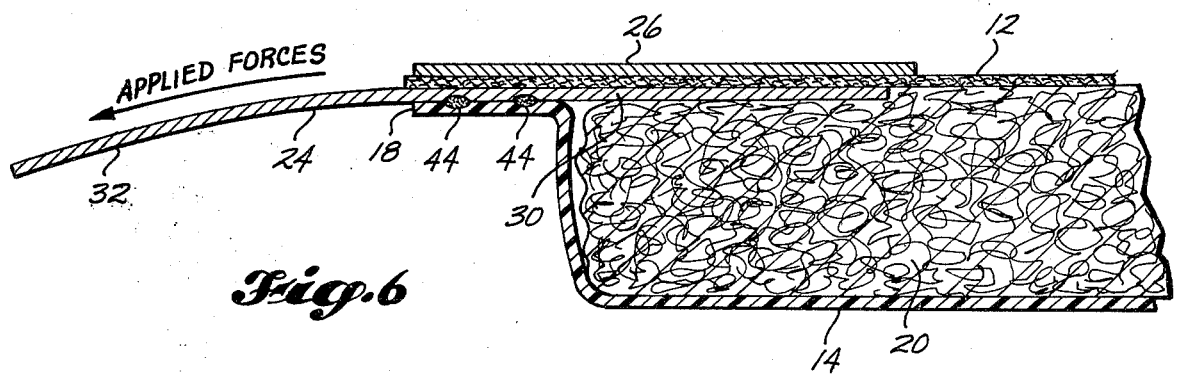
FIG. 6 is a view similar to FIG. 3 showing the attachment portion of the alternate tape fastener structure in a stressed condition.

Turning now to FIGS. 4-6, wherein like reference numbers will represent like elements, a description of an alternate embodiment of the present invention will be given. The cutaway corner section of disposable diaper 40 is depicted in FIG. 4. Diaper 40 is substantially similar to disposable diaper 10 in FIGS. 1-3, but in diaper 40 the filler material 20 does not extend laterally to the side edges of the diaper, but rather terminates at a position inwardly from the side edges 18 where the bottom surface of the top sheet 12 and backing sheet 14 are fixedly bonded together along two-layer marginal side portions 42. The side marginal bonding means 44 serve to hold the backing sheet to the top layer and thereby confine the filler material 20 within its intended boundaries.

Turning now to FIGS. 5 and 6, the tape fasteners 22 are again comprised of two parts. The fixed portion 30 of each fastening tape 24 underlies the marginal side edge of the top sheet 12 interposed between top sheet 12 and backing sheet 14 and is adhesively bonded to the top sheet 12 in a fixed relationship. The adhesive bonding means 44 extend along the bottom surface of the fixed portions 30 and serve to hold the marginal side edge of the plastic backing sheet material in a juxtaposed fixed relationship with each fixed portion 30. Again, when the attachment portions 32 are in their closed positions, they are folded over 180° so as to overlie the release surface of the respective release liner 26. Release liners 26 are adhesively bonded to the top surface of top sheet 12 at their normal positions.

In FIG. 6 a stressed condition is indicated by a force vector being directed outwardly along attachment portion 32. When the individual is ready to begin the diapering process, the attachment portions 32 are again peeled away from release liners 26 and extended outwardly therefrom, exerting the force as indicated. During diapering and when in use, the forces are effectively transmitted through the adhesively bonded joint between the fixed portion of the fastening tape and the bottom surface of top sheet 12 to the top sheet material where they are accepted by the stronger top sheet material. This structure also virtually eliminates tearing or rupturing of the backing sheet material during normal in-use forces.

While several preferred embodiments of the present invention have been described, it is to be understood that additional changes and modifications may be made without departing from the scope of the invention. All such modifications are intended to be included within the scope of the appended claims.

What is claimed is:

1. In an absorbent article of the type having a fluid-permeable body contacting top sheet, a fluid-impermeable plastic film backing sheet, and an absorbent filler disposed therebetween together with a tape fastener system along at least one edge of the article, the improvement comprising:
    at least one fastening tape having a fixed portion with one surface thereof being bonded to a portion of the bottom surface of the top sheet and the other surface thereof bonded to a portion of the backing sheet and an attachment portion having an open and closed position, and in which said portion of the backing sheet to which the fixed portion is bonded is a narrow marginal portion thereof which extends inwardly from the article edge after having extended around said edge and in a plane substantially coplaner with the top sheet and said fastening tape, when in the open position, serving to transmit a substantial amount of the forces applied thereto through the bonded area between the fixed portion and a portion of the bottom surface of the top sheet to the top sheet.

2. The improvement as in claim 1 further including a release liner fixed to at least a portion of the top sheet in a position whereby the attachment portion of the tape can overlay at least part of the release liner in its closed position.

* * * * *